United States Patent [19]

Ogawa et al.

[11] Patent Number: 4,547,377
[45] Date of Patent: Oct. 15, 1985

[54] STABILIZED SOLID COMPOSITIONS

[75] Inventors: Hiroe Ogawa, Kobe; Yoshisuke Imamura, Kawanishi, both of Japan

[73] Assignee: Takeda Chemical Industries, Ltd., Osaka, Japan

[21] Appl. No.: 476,154

[22] Filed: Mar. 17, 1983

[30] Foreign Application Priority Data

Mar. 25, 1982 [JP] Japan ................................ 57-48234

[51] Int. Cl.[4] .......................... A23L 1/272; A23J 3/00
[52] U.S. Cl. .................................. 426/268; 426/321; 426/324; 426/334; 426/654; 426/656; 426/658; 426/661
[58] Field of Search ............... 426/268, 270, 321, 324, 426/654, 656, 661, 334, 658

[56] References Cited

U.S. PATENT DOCUMENTS

| | | | |
|---|---|---|---|
| 3,627,543 | 12/1971 | Epstein | 426/268 X |
| 3,872,020 | 3/1975 | Yamagishi et al. | 426/268 X |
| 4,144,357 | 3/1979 | Mohammed | 426/656 X |
| 4,298,601 | 11/1981 | Howard | 426/656 X |
| 4,371,557 | 2/1983 | Oppy et al. | 426/321 |

FOREIGN PATENT DOCUMENTS

| | | | |
|---|---|---|---|
| 47-14890 | 5/1972 | Japan | 426/268 |
| 68378 | 6/1981 | Japan | 426/321 |
| 34034 | 8/1981 | Japan | 426/656 |
| 100179 | 6/1982 | Japan | 426/268 |
| 79962 | 5/1983 | Japan | 426/268 |

Primary Examiner—Robert Yoncoskie
Attorney, Agent, or Firm—Wegner & Bretschneider

[57] ABSTRACT

A solid composition containing a monosaccharide or-/and a disaccharide and an amino acid is stabilized by incorporating therein at least 40%, based on said amino acid, of a polysaccharide with a water content of not more than 3%.

16 Claims, No Drawings

STABILIZED SOLID COMPOSITIONS

This invention relates to the stabilization of solid compositions. More particularly, this invention relates to the stabilization of a solid composition containing a monosaccharide or/and a disaccharide and at least one amino acid.

A solid composition containing monosaccharide or/and disaccharide and amino acid, particularly a powdery composition containing them, is known to undergo browning and caking, due to the interaction of saccharide with amino acid, and in the food and pharmaceutical industries, for instance, there has been a long-standing need to establish a technology for preventing and arresting such browning and caking phenomena.

Under the technical circumstances the present inventors conducted an intensive research and unexpectedly found that both the browning and caking phenomena could be substantially prevented by incorporating in such a solid composition at least 40% (weight/weight) [hereinafter all the percent is expressed as weight/weight percent] of a polysaccharide with a water content of not more than 3%, relative to said amino acid. The finding was followed by further studies which have resulted in the accomplishment of this invention.

Thus, this invention provides a method of stabilizing a solid composition characterized by incorporating in a solid composition containing a monosaccharide or/and a disaccharide and an amino acid at least 40%, based on said amino acid, of a polysaccharide with a water content of not more than 3%, and also to a solid composition thus stabilized.

The stabilizing method of this invention is applicable to any solid composition containing optional kinds of monosaccharide or/and disaccharide and amino acid that would otherwise undergo browning or/and caking. Said monosaccharide may be any of tetroses, pentoses and hexoses, and is exemplified by erythrose, threose, ribose, xylose, arabinose, glucose, fructose, mannose, galactose, etc. As examples of said disaccharide may be mentioned sucrose, lactose, maltose, etc. Particularly preferred species of these saccharides are glucose, fructose, xylose, galactose, sucrose, lactose, maltose, etc. Only one member of these monosaccharides and disaccharides may be present in said solid composition or two or more members of them may be present. (Hereinafter, these monosaccharides or/and disaccharides will be referred to briefly as "sugar".)

The amino acid may be any of aliphatic amino acids such as monoaminomonocarboxylic acids (glycine, alanine, valine, leucine, isoleucine, etc.), hydroxyamino acids (serine, threonine, etc.), sulfur-containing amino acids (cysteine, cystine, methionine, etc.), monoaminodicarboxylic acids (aspartic acid, glutamic acid, etc.), diaminomonocarboxylic acids (lysine, arginine, etc.), amino acids containing an aromatic nucleus (tyrosine, phenylalanine, etc.), and amino acids containing a heterocyclic ring (histidine, tryptophan, proline, hydroxyproline, etc.). These amino acids may be in the form of salts with physiologically acceptable bases or acids. Said bases include inorganic bases such as alkali metals (sodium, potassium, etc.), and alkaline earth metals (calcium, barium, etc.), and said acids include mineral acids such as hydrochloric acid, sulfuric acid, phosphoric acid, etc. and organic acids such as acetic acid, lactic acid, fumaric acid, tartaric acid, citric acid, gluconodeltalactone, gluconic acid, malic acid, etc. Among these amino acids, glycine, alanine, methionine, aspartic acid and its sodium salt, and glutamic acid and its sodium salt are particularly suitable. Either one member or more members than one such amino acid may be present in said solid composition.

The polysaccharide is preferably composed of at least 4 monosaccharide units, such as starch, cellulose, dextran, pullulane, agar, pectin, konniyaku mannan, starch phosphate ester sodium, arabinogalactan, dextrin, cyclodextrin, etc. Particularly preferred are those consisting of glucose units and, for example, starch, pullulane, dextrin, cyclodextrin, etc. are advantageous. It is especially advantageous to use dextrin.

In accordance with this invention, the above-mentioned polysaccharide, in a state containing not more than 3% of water and in a proportion of at least 40% relative to the amino acid, is incorporated in said solid composition containing the sugar and amino acid, whereby said browning and caking are effectively prevented. Particularly, the browning and caking can be prevented very remarkably by adding the polysaccharide in a state containing not more than 2% and, especially, not more than 1% of water. Such stabilizing effect cannot be accomplished with the polysaccharide whose water content is in excess of 3% which is the usual level.

Relative to the total weight of amino acids in the composition, the polysaccharide is desirably incorporated in a proportion of about 40 to 800%, preferably 60 to 700% and for still better results, 90 to 500%.

To incorporate the polysaccharide with a water content of not more than 3%, preferably not more than 2% and more desirably not more than 1% in said solid composition, the water content of the polysaccharide may be previously adjusted to the defined level before addition to the solid composition or the polysaccharide with an usual water content is added to the solid composition and the mixture subsequently dehydrated to a water level of not more than 3%, preferably not more than 2% or more desirably not less than 1%. In incorporating the polysaccharide, it is advantageous to admix the polysaccharide with the sugar, amino acid and other components to be incorporated in the desired solid composition, all in powdery form. It is generally advisable to prepare each component in suitable grain size before admixing. It is especially advantageous to evenly compound the components after passing them through a mesh of 42 mesh size (mesh size referred to in "Japan Industrial Standard Z 8801-1976", the same applies hereinafter) or less, especially a mesh of 60 mesh size. When particles in excess of 42 mesh are employed, it is desirable to prepare them to a uniform size. The composition after addition of the polysaccharide may be granulated or tableted by the conventional procedure, if desired. The resulting preparation is substantially free from both the borwning and caking tendencies.

In the practice of this invention, a more pronounced stabilizing effect can be realized by maintaining the polysaccharide-containing composition under conditions that will substantially prevent ingress of water into the composition. Particularly, under high temperature, high humidity conditions, the composition is desirably encased or otherwise sealed against the external environment as soon as possible after compounding. For this purpose, it is advantageous to package the composition gas-tight using a gas-impermeable or sparingly gas-permeable packaging material such as a plastic sheet, a glass container, polyvinyl chloride, polypropylene, cellophane or polyvinylidene chloride copolymer film, or a suitable laminate material, to name but a few. In case a relatively permeable material such as polyethylene is used as said packaging material, it is desirable to use one having a comparatively large thickness.

The preparation and packaging of the solid composition according to this invention are preferably conducted in an environment at a relative humidity of not more than 70%, preferably not more than 60%, and a temperature of not higher than 30° C., preferably not higher than 25° C.

The stable composition according to this invention may contain optional components in addition to the sugar, amino acid and polysaccharide according to the intended use. Such additional components may for example be a variety of flavorants (e.g. sweeteners such as saccharin, saccharin sodium, glycyrrhizin, stevioside, etc.), medicaments, salts, preservatives, fungicides, volume builders, etc. The reaction between sugar and amino acid is promoted by the presence of electrolytes such as salts, especially acetates (e.g. sodium acetate, potassium acetate, etc.), carbonates (e.g. sodium carbonate, magnesium carbonate, calcium carbonate, etc.) or hydrogen carbonates (e.g. sodium hydrogen carbonate, etc.) but this invention is effective enough to stabilize even a composition containing about 1 to 20%, and particularly 3 to 15%, of acetate, carbonate or/and hydrogen carbonate.

This invention is applicable to a broad range of sugar- and amino acid-containing solid compositions and especially to sugar-and amino acid-containing powdery compositions such as powdery foods, condiments, juices, drugs for humans, veterinary drugs, feed additives, feeds and so on and as it attains a significant inhibition of browning and caking of such compositions during production, storage, transit and distribution, it is of great commercial value. Particularly, this invention provides a very remarkable stabilization of a powdery electrolyte modifier for animal use which contains glucose, glycine and electrolytes such as sodium chloride, monopotassium phosphate, sodium citrate, magenesium sulfate and sodium hydrogen carbonate.

The effectiveness of this invention will hereinafter be described in detail by way of experimental and working examples, it being, however, to be understood that the invention is by no means limited thereto. It should also be noted that the production and packaging of solid compositions in the following experimental and working examples were conducted at a relative humidity of 50 to 60% and a temperature of 13° to 20° C. unless otherwise specified.

Throughout the present specification as well as in claims, the abbreviations "g", "l", "°C." and "R.H." respectively refer to "grams(s)", "liter(s)", "degree(s) centigrade" and "relative humidity", and percent is weight/weight percent unless otherwise specified.

EXPERIMENTAL EXAMPLE 1

(1) Test Method

Fifty parts (by weight, the same applies hereinafter) of anhydrous glucose, 50 parts of glycine and, based on the glycine, 30, 40, 60, 80 or 100% of dry dextrin (water content 1.5%), all components having been passed through a mesh of 60 mesh size, were evenly compounded and packaged gas-tight in a laminate bag. Each of the bags was stored in an incubator maintained at 40° C. and 80% R.H. and the content was compared with a control preparation which did not contain dextrin as to the degrees of browning and caking.

(2) Results

The results of the above experiment are shown in Table 1. The sample containing 40% of dextrin relative to glycine was superior to control, and the preparations containing 60, 80 and 100% of dextrin were very stable without showing any appreciable browning or caking even after 25 days of storage. In the table, − denotes no browning, ± faint browning, + through ∓ various degrees of browning. (The like legends hereinafter mean the like effects.)

TABLE 1

| Composition (parts) | | | Amount of dextrin relative to glycin (%) | Stability as the lapse of storage days | | | | | | | |
|---|---|---|---|---|---|---|---|---|---|---|---|
| Anhydrous glucose | Glycine | Dextrin | | 3 | 5 | 10 | 13 | 20 | 25 | 30 | 40 |
| 50 | 50 | 0 | 0 | + | + | ++ | ++ | | | | |
| 50 | 50 | 15 | 30 | − | − | ± | + | ++ | | | |
| 50 | 50 | 20 | 40 | − | − | − | ± | ± | + | + | ++ |
| 50 | 50 | 30 | 60 | − | − | − | − | − | ± | ± | + |
| 50 | 50 | 40 | 80 | − | − | − | − | − | − | − | ± |
| 50 | 50 | 50 | 100 | − | − | − | − | − | − | − | − |

EXPERIMENTAL EXAMPLE 2

(1) Test Method

Forty parts of anhydrous glucose were compounded with 5, 10 or 15 parts of glycine and, based on the glycine, 40, 60, 80 or 100% of dry dextrin (water content 2%), all components having been passed through a mesh of 60 mesh size, and each of the resulting compositions was tested by the same procedure as Experimental Example 1. For the purpose of promoting browning, 10 parts of sodium carbonate (anhydrous) was added to the composition.

(2) Results

The results of the above experiment are shown in Table 2. The samples containing 40, 60, 80 or 100% of dextrin relative to glycine showed excellent stability despite the quantitative variation of glycine relative to glucose and the presence of sodium carbonate.

TABLE 2

| Classification | Composition (parts) | | | | Amount of glycine relative to dextrin (%) | Stability as the lapse of storage days | | | | | | | |
|---|---|---|---|---|---|---|---|---|---|---|---|---|---|
| | Anhydrous glucose | Glycine | Sodium Carbonate | Dextrin | | 4 | 5 | 7 | 10 | 15 | 20 | 25 | 30 | 40 |
| Control | 40 | 5 | 10 | 0 | 0 | − | ± | ± | + | + | ++ | | | |

TABLE 2-continued

| Classification | Composition (parts) | | | | Amount of glycine relative to dextrin (%) | Stability as the lapse of storage days | | | | | | | | |
|---|---|---|---|---|---|---|---|---|---|---|---|---|---|---|
| | Anhydrous glucose | Glycine | Sodium Carbonate | Dextrin | | 4 | 5 | 7 | 10 | 15 | 20 | 25 | 30 | 40 |
| This invention | 40 | 5 | 10 | 2 | 40 | − | − | − | − | − | ± | ± | + | ++ |
| This invention | 40 | 5 | 10 | 3 | 60 | − | − | − | − | − | − | − | ± | + |
| This invention | 40 | 5 | 10 | 4 | 80 | − | − | − | − | − | − | − | − | ± |
| This invention | 40 | 5 | 10 | 5 | 100 | − | − | − | − | − | − | − | − | − |
| Control | 40 | 10 | 10 | 0 | 0 | − | + | + | + | ++ | | | | |
| This invention | 40 | 10 | 10 | 4 | 40 | − | − | − | − | − | ± | + | ++ | |
| This invention | 40 | 10 | 10 | 6 | 60 | − | − | − | − | − | − | − | ± | + |
| This invention | 40 | 10 | 10 | 8 | 80 | − | − | − | − | − | − | − | − | + |
| This invention | 40 | 10 | 10 | 10 | 100 | − | − | − | − | − | − | − | − | − |
| Control | 40 | 15 | 10 | 0 | 0 | ± | + | + | ++ | ++ | | | | |
| This invention | 40 | 15 | 10 | 6 | 40 | − | − | − | − | − | + | + | ++ | |
| This invention | 40 | 15 | 10 | 9 | 60 | − | − | − | − | − | − | ± | + | ++ |
| This invention | 40 | 15 | 10 | 12 | 80 | − | − | − | − | − | − | − | − | + |
| This invention | 40 | 15 | 10 | 15 | 100 | − | − | − | − | − | − | − | − | − |

EXPERIMENTAL EXAMPLE 3

(1) Test Method

Forty parts of anhydrous glucose, 15 parts of glycine and 10 parts of sodium carbonate (anhydrous) and dextrin having a varying water content of 1%, 2%, 3%, or 4%, all component having been passed through a mesh of 60 mesh size, were admixed and the stability of the resulting mixtures was determined by the same procedure as Experimental Example 1. Dextrin was incorporated in a proportion of 100% relative to glycine.

(2) Results

The results of the above experiment are shown in Table 3. While the sample containing 4% of water was not much different from the control (without dextrin), the samples containing 3% or less, particularly one containing 1% of water, exhibited excellent stability.

TABLE 3

| Classification | Composition (parts) | | | | Water content of dextrin (%) | Stability as the lapse of storage days | | | | | | | | |
|---|---|---|---|---|---|---|---|---|---|---|---|---|---|---|
| | Anhydrous glucose | Glycine | Sodium carbonate | Dextrin | | 4 | 5 | 6 | 10 | 15 | 20 | 25 | 30 | 40 |
| Control | 40 | 15 | 10 | — | — | ± | + | + | ++ | ++ | | | | |
| Control | 40 | 15 | 10 | 15 | 4 | − | − | ± | + | + | ++ | | | |
| This invention | 40 | 15 | 10 | 15 | 3 | − | − | − | − | ± | ± | + | + | ++ |
| This invention | 40 | 15 | 10 | 15 | 2 | − | − | − | − | − | − | − | − | ± |
| This invention | 40 | 15 | 10 | 15 | 1 | − | − | − | − | − | − | − | − | − |

EXPERIMENTAL EXAMPLE 4

(1) Test Method

Thirty parts of fructose, 30 parts of L-aspartic acid and, based on the aspartic acid, 20, 30, 40, 50 or 100% of purified and sterilized dry corn starch (water content 1%) were respectively passed through a mesh of 60 mesh size and admixed. The stability of these compositions was determined by the same procedure as Experimental Example 1. For the purpose of promoting discoloration, 10 parts of sodium acetate (anhydrous) was added to each composition.

(2) Results

The results of the above experiment are shown in Table 4. The sample containing 40% of purified and sterilized dry corn starch relative to L-aspartic acid was superior to control and the sample containing 50% of corn starch was still better. The sample containing 100% exhibited excellent stability without showing any discoloration even after 30 days of storage.

TABLE 4

| Composition (parts) | | | | Amount of the corn starch relative to L-aspartic acid (%) | Stability as the lapse of storage days | | | | | | |
|---|---|---|---|---|---|---|---|---|---|---|---|
| Fructose | L-aspartic acid | Sodium acetate | Purified and sterilized dry corn starch | | 2 | 5 | 7 | 10 | 15 | 20 | 30 |
| 30 | 30 | 10 | 0 | 0 | ± | + | + | ++ | ++ | | |
| 30 | 30 | 10 | 6 | 20 | − | − | ± | + | + | ++ | |
| 30 | 30 | 10 | 9 | 30 | − | − | − | ± | ± | + | ++ |
| 30 | 30 | 10 | 12 | 40 | − | − | − | − | − | ± | + |
| 30 | 30 | 10 | 15 | 50 | − | − | − | − | − | − | ± |
| 30 | 30 | 10 | 30 | 100 | − | − | − | − | − | − | − |

EXAMPLE 1

Using as a control a powdery condiment prepared by admixing 46% of sodium chloride, 26% of anhydrous glucose, 1% of disodium succinate, 0.05% of 5'-ribonucleotide sodium and 26.95% of sodium L-glutamate, each of the components having been previously passed through a mesh of 60 mesh size, a stability test was conducted by the same procedure as Experimental Example 1 on a composition prepared by adding 20 parts (96.2% based on the sodium L-glutamate) of dextrin [Pinedex®, Matsutani Chemical Co., Ltd. Itami, Japan], which had been thermally dehydrated to a water content of 0.6% and passed through a mesh of 60 mesh size, to 80 parts of the same powdery condiment as the control. The results of this test are set forth in Table 5.

The sample according to this invention exhibited excellent stability without showing any discoloration even after 20 days of storage.

TABLE 5

| Classification | Stability as the lapse of storage days | | | | | |
|---|---|---|---|---|---|---|
| | 2 | 4 | 8 | 12 | 15 | 20 |
| Control | − | ± | + | + | + | ++ |
| This Invention | − | − | − | − | − | − |

EXAMPLE 2

(1) Using as a control a powdery condiment (for pickles) prepared by admixing 44.5% of sodium L-glutamate, 10% of glycine, 2% of DL-alanine, 1.5% of succinic acid, 0.5% of citric acid (anhydrous) and 41.5% of fructose, each of the components having been passed through a mesh of 60 mesh size, a stability test under the same conditions as that described in Experimental Example 1 was conducted on a composition prepared by adding 20 parts (44.2% relative to the total amount of sodium L-glutamate, glycine and DL-alanine) of purified and sterilized dry starch with a water content of 0.8% to the same condiment as the control. The results are shown in Table 6. It is apparent that the composition of this invention exhibited excellent stability as compared with the control.

TABLE 6

| Classification | Stability as the lapse of storage days | | | | | |
|---|---|---|---|---|---|---|
| | 2 | 5 | 10 | 14 | 17 | 20 |
| Control | ± | + | + | + | ++ | ++ |
| This invention | − | − | − | − | ± | ± |

(2) Twenty-five % of sodium glutamate, 2% of 5'-ribonucleotide sodium, 1% of 5'-guanylic acid, 1% of disodium succinate, 5% of glycine, 5% of DL-alanine, 10% of anhydrous glucose, 3% of sodium citrate and 48% (120% relative to the total amount of sodium glutamate, DL-alanine and glycine) of dry dextrin with a water content of 0.8%, each of them having been passed through a mesh of 60 mesh size, were evenly compounded at 15.6° C. and at 55% R.H. to prepare a powdery condiment (for pickles).

100 g Portion each of thus prepared condiment was rapidly packaged gas-tight in a bag of laminate consisting of 12μ polyester film, 13μ polyethylene film, 9μ aluminum laminate and 40μ polyethylene film, and stored under atmospheric conditions at room temperature (15° C. to 30° C.) for 6 months, at the end of which time there was appreciated neither browning nor caking.

EXAMPLE 3

(1) Using as a control a powdered juice (soft drink) prepared by admixing 40% of anhydrous glucose, 15% of glycine, 8% of DL-alanine, 34.094% of sucrose, 0.006% of vitamin $B_1$, 1.1% of sodium chloride, 1.1% of potassium chloride, 0.6% of disodium phosphate (anhydrous) and 0.1% of magnesium chloride, each of the components having been passed through a mesh of 60 mesh size, a stability test under the same conditions as that described in Experimental Example 1 was conducted on a composition prepared by adding 20 parts (108.7% based on the combined amount of glycine and DL-alanine) of β-cyclodextrin thermally dehydrated to a water content of 0.8% and passed through a mesh of 60 mesh size to 80 parts of the same powdered juice as the control. The results of the above test are shown in Table 7. It is apparent that whereas the control juice underwent browning and caking within a day after preparation, the composition according this invention exhibited excellent stability both in terms of discoloration and in terms of caking.

TABLE 7

| Classification | Item of observation | Stability | | | | | |
|---|---|---|---|---|---|---|---|
| | | Storage days | | | | | |
| | | 1 | 4 | 7 | 10 | 16 | 20 |
| Control | Browning | ± | ++ | +++ | +++ | | |
| | Caking* | ± | + | + | ++ | | |
| This invention | Browning | − | − | − | − | ± | ± |
| | Caking* | − | − | − | − | − | − |

*denotes no caking,
± slightly caking,
+ through
+++ various degrees of caking.

(2) Five % of sodium aspartate, 8% of glycine, 2% of DL-methionine, 1% of potassium chloride, 0.5% of magnesium sulfate (anhydrous), 31% of anhydrous glucose, 6% of purified stevioside, 3% of purified glycyrrhizin, 3.5% of disodium phosphate (anhydrous) and 40% (266% relative to the combined amount of sodium L-asparate, DL-methionine and glycine) of dry dextrin with a water content of 0.8%, each of them having been passed through a mesh of 60 mesh size, were evenly admixed at 15.0° C. and at 65% R.H. to obtain a powdery juice (soft drink).

100 g portion each of thus prepared powdery juice was rapidly packaged gas-tight in a bag of the laminate mentioned in Example 2.-(2), and stored under atmospheric conditions at room temperature (15° C. to 30° C.) for 6 months, at the end of which time there was appreciated neither browning nor caking.

EXAMPLE 4

(1) Using as a control an electrolyte modifier for animal use prepared by admixing 47.39% of anhydrous glucose, 23.70% of glycine, 11.85% of sodium chloride, 7.11% of monopotassium phosphate, 4.74% of cirtic acid (anhydrous), 0.47 of magnesium sulfate (anhydrous) and 4.74% of sodium hydrogen carbonate, each of the components having been passed through a mesh of 60 mesh size, a stability test under the same conditions as that described in Experimental Example 1 was conducted on a composition by adding 100%, based on glycine, of dextrin [Pinedex] theramlly dehydrated to a water content of 0.7% and passed through a mesh of 60 mesh size to the same electrolyte modifier as the control. As set forth in Table 8, the composition of this invention displayed excellent stability.

The control was dehydrated to a water content of 1% or less before gas-tight packaging.

TABLE 8

| Classification | Stability as the lapse of storage days | | | | | | |
|---|---|---|---|---|---|---|---|
| | 4 | 7 | 10 | 12 | 16 | 20 | 30 |
| Control | ± | + | + | ++ | ++ | +++ | +++ |
| This invention | − | − | − | − | − | − | − |

It is apparent that this invention provides a remarkable stabilization of the electrolyte modifier for animal use which consists of glucose, glycine and the electrolytes. The electrolyte modifier for animal use thus stabilized can be put to use in exactly the same manner as the conventional electrolyte modifier for animal use. For example, by dissolving it in water and administering the resulting solution to domestic animals, diarrhea in them can be prevented and cured.

(2) Thirty-six % of anhydrous glucose, 15.0% of glycine, 11.7% of sodium chloride, 2.3% of monopotassium phosphate, 8.6% of sodium citrate (anhydrous), 1.0% of magnesium sulfate (anhydrous), 8.4% of sodium hydrogen carbonate and 17.0% (113.3% relative to glycine) of dry dextrin with a water content of 0.8%, each of them having been passed through a mesh of 60 mesh size, were evenly compounded at 25° C. and at 60% R.H. to prepare a powdery electrolyte modifier for animal use.

60 g Portion each of thus prepared electrolyte modifier was rapidly packaged gas-tight in a bag of the laminate mentioned in Example 2.-(2), and stored under atmospheric conditions at room temperature (15° C. to 30° C.) for 6 months, at the end of which time there was appreciated neither browning nor caking.

60 g Portion each of thus stabilized powdery electrolyte modifier is dissolved in 2l of water and orally administered ad libitum to domestic animals, especially calves, suffered from diarrhea.

EXAMPLE 5

Using as a control a powdered juice (soft drink) prepared by blending 55% of anhydrous glucose, 5% of sodium hydrogen carbonate, 3% of sodium L-aspartate, 5% of DL-alanine, 24.1% of sucrose, 1.1% of sodium chloride, 1.1% of potassium chloride, 0.6% of disodium phosphate (anhydrous), 0.1% of magnesium chloride and 5% of citric acid (anhydrous), each of the components having been passed through a mesh of 60 mesh size, a stability test under the same conditions as that described in Experimental Example 1 was conducted on a composition prepared by adding 20 parts (312.5% based on the combined amount of sodium L-aspartate and DL-alanine) of $\beta$-cyclodextrin thermally dehydrated to a water content of 0.3% and passed through a mesh of 60 mesh size to the same juice as the control. The results are shown in Table 9. It is apparent that the composition according to this invention exhibited excellent stability without showing any discoloration or caking at all even after 20 days.

TABLE 9

| Classification | Iterm of observation | Stability Storage days | | | | | | |
|---|---|---|---|---|---|---|---|---|
| | | 2 | 4 | 8 | 11 | 15 | 20 | 30 |
| Control | Browning | − | ± | + | ++ | ++ | +++ | +++ |
| | Caking | ± | ± | + | + | + | ++ | ++ |
| This invention | Browning | − | − | − | − | − | − | − |
| | Caking | − | − | − | − | − | − | − |

What is claimed is:

1. A powdery human food or animal feed composition stabilized against caking and browning which comprises a physical mixture of separate components of one or more sugars selected from the group consisting of monosaccharides and disaccharides and one or more amino acids, in which said amino acids and sugars are present in amounts sufficient to produce caking and browning, and, based on the content of said amino acids, at least 40% by weight of one or more polysaccharides, said polysaccharides having a water content of not more than 3%, said polysaccharides in said composition being in amounts sufficient to prevent both caking and browning.

2. A composition of claim 1, wherein the polysaccharide is composed of at least 4 monosaccharide units.

3. A composition of claim 2, wherein the monosaccharide unit is a glucose unit.

4. A composition of claim 1, wherein the polysaccharide is starch, pullulane, dextrin or cyclodextrin.

5. A composition of claim 1, wherein the polysaccharide has a water content of not more than 1%.

6. A composition of claim 1, wherein the amount of the polysaccharide is about 60% to 700% relative to the amino acid member.

7. A composition of claim 1, wherein the amount of the polysaccharide is about 90% to 500% relative to the amino acid member.

8. A composition of claim 1, wherein the monosaccharide is tetrose, pentose or hexose.

9. A composition of claim 1, wherein the sugar is glucose, fructose, xylose, galactose, sucrose, lactose or maltose.

10. A composition of claim 1, wherein the amino acid is glycine, alanine, methionine, aspartic acid, glutamic acid or a sodium salt of them.

11. A composition of claim 1, which one or more electrolytes.

12. A composition of claim 11, the electrolyte is acetate, carbonate or hydrogen carbonate.

13. A composition of claim 1, which contains glucose as the sugar, glycine as the amino acid, dextrin as the polysaccharide and one or more electrolytes.

14. A composition of claim 11, wherein the electrolytes are sodium chloride, monopotassium phosphate, sodium citrate, magnesium sulfate and sodium hydrogen carbonate.

15. A composition of any one of claims 1, which is in a gas tight packaged unit usage form.

16. A method of stabilizing a powdery human food or animal feed composition against caking and browning comprising one or more sugars selected from the group consisting of monosaccharides and disaccharides and one or more amino acids, in which said amino acids and sugars are present in amounts sufficient to produce caking and browning, which comprises incorporating in said powdery composition to form a physical mixture of separate components at least 40% by weight, based on the amino acid content, of one or more polysaccharides, said polysaccharides having a water content of not more than 3%, said polysaccharides in said composition being in amounts sufficient to prevent both caking and browning.

* * * * *

UNITED STATES PATENT AND TRADEMARK OFFICE
CERTIFICATE OF CORRECTION

PATENT NO. : 4,547,377

DATED : October 15, 1985

INVENTOR(S) : Hiroe Ogawa et al.

It is certified that error appears in the above-identified patent and that said Letters Patent is hereby corrected as shown below:

On the title page:

Item No. [73] should read: "Assignee: Takeda Chemical Industries, Ltd., Osaka, Japan, part interest".

Signed and Sealed this

Third Day of June 1986

[SEAL]

*Attest:*

DONALD J. QUIGG

*Attesting Officer*     *Commissioner of Patents and Trademarks*